United States Patent [19]
Rohdewald

[11] Patent Number: 5,720,956
[45] Date of Patent: Feb. 24, 1998

[54] METHOD OF CONTROLLING THE REACTIVITY OF HUMAN BLOOD PLATELETS BY ORAL ADMINISTRATION OF THE EXTRACT OF THE MARITIME PINE (PYCNOGENOL)

[76] Inventor: Peter Rohdewald, Schulze-Isforstr. 4, D-48341 Altenberge, Germany

[21] Appl. No.: 631,738

[22] Filed: Apr. 10, 1996

[51] Int. Cl.[6] ............................................. A61K 35/78
[52] U.S. Cl. .................... 424/195.1; 514/456; 514/822
[58] Field of Search ..................... 424/195.1; 514/456, 514/822

[56] References Cited

U.S. PATENT DOCUMENTS 4,698,360  10/1987  Masquelier .............................. 514/456

*Primary Examiner*—John W. Rollins
*Attorney, Agent, or Firm*—Nikaido Marmelstein Murray & Oram LLP

[57] ABSTRACT

A method of inhibiting platelet aggregation with an agent which is able to normalize and enhance platelet reactivity without adversely affecting the bleeding time. The method additionally prevents adrenaline-induced platelet aggregation.

5 Claims, 2 Drawing Sheets

METHOD OF CONTROLLING THE REACTIVITY OF HUMAN BLOOD PLATELETS BY ORAL ADMINISTRATION OF THE EXTRACT OF THE MARITIME PINE (PYCNOGENOL)

The present invention relates to a method of controlling human blood platelets reactivity.

Platelet aggregation is a major contributing factor to a great variety of cardiovascular diseases. In the pathogenesis of arteriosclerosis, besides lesions of the endothelium, the activation of platelet aggregation leading to the adhesion of platelet aggregates to the vascular wall is one of the first steps in thrombus formation.

Consequently, inhibition of platelet aggregation is applied in stroke prophylaxis. Therefore, acetylsalicylic acid (ASA), a well-known inhibitor of platelet aggregation has been successfully tested in clinical trials for the prevention of arterio-thrombotic, cerebral or myocardial infarction. ASA was found to reduce the number of infarctions in volunteers and in high-risk patients, too. In a subpopulation of patients platelet aggregation could not be prevented by ASA. One reason for the lack of the anti-thrombotic effect of ASA in those patients might be the fact that adrenaline is able to induce platelet aggregation even in presence of ASA. Since adrenaline is produced under stress, non-responders to ASA anti-thrombotic prophylaxis may be under greater continuous stress than responders.

A high risk factor for cardiovascular diseases is smoking. Smoking increases platelet reactivity, and it has been demonstrated that nicotine induces thrombus formation. Besides nicotine or, additionally, the tar fraction of smoke may also produce increased platelet reactivity.

It has been demonstrated that ASA is able to reduce the enhanced platelet aggregation following smoking. However, in this case as well ASA could not prevent the smoking-induced enhancement of platelet function in men with coronary heart diseases.

Therefore, it seems that the action mechanism of ASA, i.e. the irreversible acetylation of cyclooxygenase, cannot inhibit platelet aggregation in each case.

Besides these cases of lacking prevention the side effects of regular intake of ASA are not totally insignificant, even when relatively low doses are applied. Gastric bleedings and allergic reactions like ASA-induced asthma or even serious dermatological reactions like Lyell's syndrome must be taken into consideration.

If it were possible to inhibit platelet aggregation by a substance preventing increased platelet reactivity, however, without producing bleedings or allergic asthma, the benefit-risk ratio in the prophylaxis of infarctions would be improved. An additional advantage would be achieved by a substance inhibiting adrenaline-induced platelet aggregation.

It is therefore an object of the present invention to provide an agent which is able to normalize an enhanced platelet reactivity without adversely affecting the bleeding time as a measure of bleeding tendency. A further object of the invention is to provide an agent which does not only normalize platelet reactivity to the same extent as ASA— tested on the model of smoking-induced platelet reactivity— but, additionally, prevents adrenaline-induced platelet aggregation.

Still another object is to provide a method of controlling human blood platelet reactivity, especially by inhibition of adrenaline-induced platelet aggregation. These objects are achieved by the method of administering an extract of the bark of the maritime pine, *Pinus maritima*, to a human being for controlling platelet aggregation. Said extract of the bark of the maritime pine is in the following referred to as Pycnogenol™.

Pycnogenol™ contains procyanidines consisting of catechin and epicatechin units linked by C-C bonds to form dimers, trimers and other oligomers up to a chain length of 6–7 molecules and phenolic acids and its glucose derivatives (1). Pycnogenol™ is produced according to U.S. Pat. No. 4,698,360 which is incorporated herein for reference. The extract used according to the invention may be prepared essentially by extracting maritime pine bark in comminuted form with boiling water, saturating the filtered extract with sodium chloride or, alternatively, adding ammonium sulfate to 20% w/v, separating the precipitate formed, repeatedly extracting the supernatant with 1/10 volume of ethyl acetate, drying the collected ethyl acetate extracts, concentrating the dried extract, pouring it into 3 volumes of chloroform with stirring and collecting the precipitate which may be purified by repeating the dissolution in ethyl acetate and precipitation with chloroform. Other extraction methods leading to the same composition of the extract may also be used to prepare this extract.

Procyanidins normalize in vitro platelet aggregation, the effects are comparable with ASA. The inhibitory effect on platelet aggregation might be explained by the fact that thromboxane biosynthesis is inhibited by procyanidins in cell free systems and in intact platelets (2). Pycnogenol™ can be used as an agent in animals or humans to tighten capillaries so that edema formation is prevented (3,4).

Furthermore, Pycnogenol™ is known to have radical scavenging activity and anti-inflammatory properties in animals (1). An inhibition of platelet reactivity in humans cannot be deduced from these properties.

The invention is based on the finding that Pycnogenol™, after oral intake, inhibits the smoking-induced enhanced platelet reactivity in humans and that Pycnogenol™ also normalizes in vitro the adrenaline-induced aggregation of human platelets.

It is known that Pycnogenol™ produces only minor side effects, such as gastro-intestinal troubles, when the extract is taken on an empty stomach. No such side effects had been reported after intake together with the meals.

The new method of use according to the present invention thus allows normalization of enhanced platelet reactivity without producing the adverse effects related to the intake of ASA, especially without affecting bleeding time, because Pycnogenol™ causes no increase in bleeding time in humans, in contrast to ASA. In contrast to the dosage of Pycnogenol™ used as a radical scavenger and anti-inflammatory agent of 100 mg daily, the dosage for the normalisation of enhanced platelet reactivity is 200–500 mg daily, preferably about 250–350 mg daily, with the single dose being about 50–150 mg. The maritime pine bark extract may be administered in dry form, e.g. tablets, coated pills, pellets, capsules, cachets or solutions prepared with common pharmaceutical solvents. Usual pharmaceutically acceptable excipients, diluents and carriers may also be used.

The invention is illustrated by the following examples in conjunction with the figures of the accompanying drawing.

EXAMPLE 1

Experiments were performed with 22 male healthy smokers; written consent and approval of the local ethical committee was obtained. 500 mg ASA or 100 mg Pycnogenol™ (extract from the bark of the maritime pine) were given as tablets 2–3 hrs before the first blood sampling at an interval of 2 weeks. A blank experiment to obtain a basic value was performed before. Immediately after a first blood sampling volunteers smoked 3 cigarettes within 30 min. Thereafter, blood sampling was repeated. 300 μl blood were suspended in both a syringe filled with EDTA buffer and in another one filled with EDTA-formaldehyde buffer. Red blood cells were counted in both samples. Whereas in the EDTA sample the activated platelets attached to each other or to red blood cells were dissolved, they remained fixed in the EDTA-formaldehyde medium. Centrifugation caused only single platelets to remain in the supernatant. Platelets were counted in both supernatants by means of a platelet counter. The platelet reactivity index (PR) was calculated as follows:

$$\frac{\text{Platelets in } EDTA \times \text{Red Blood Cells in Formalin-}EDTA}{\text{Platelets in Formalin-}EDTA \times \text{Red Blood Cells in } EDTA} = PR$$

The PR increases linearly with the number of aggregated platelets.

Figure 1:
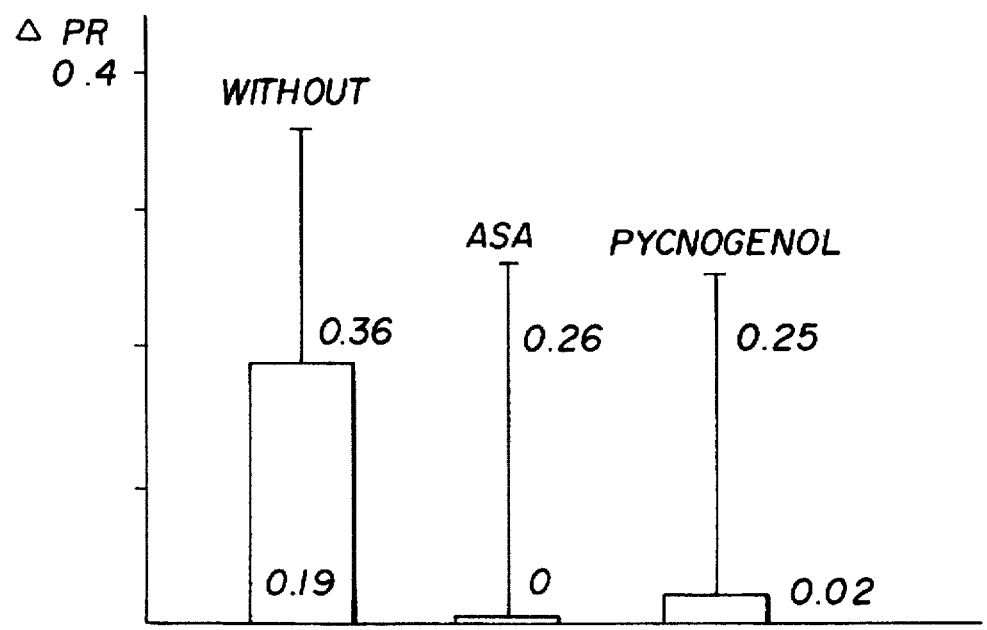
FIG. 1 is a graph showing the increase in platelet reactivity after smoking without intake of ASA and following intake of 500 mg ASA or 100 mg Pycnogenol™ demonstrating the effect of ASA as well as Pycnogenol™ by providing APR difference in platelet reactivity index to the value before smoking.

FIG. 1 shows the expected increase in platelet reactivity after smoking with standard deviations. Smoking-induced platelet aggregation was significantly normalized by ASA ($p=0.06$) and by the pine bark extract ($p=0.08$).

Hence it follows that a single dose of 100 mg Pycnogenol™ is able to normalize smoking-induced platelet aggregation to the same extent as 500 mg ASA; the slight difference between both treatments is not significant.

Figure 2:
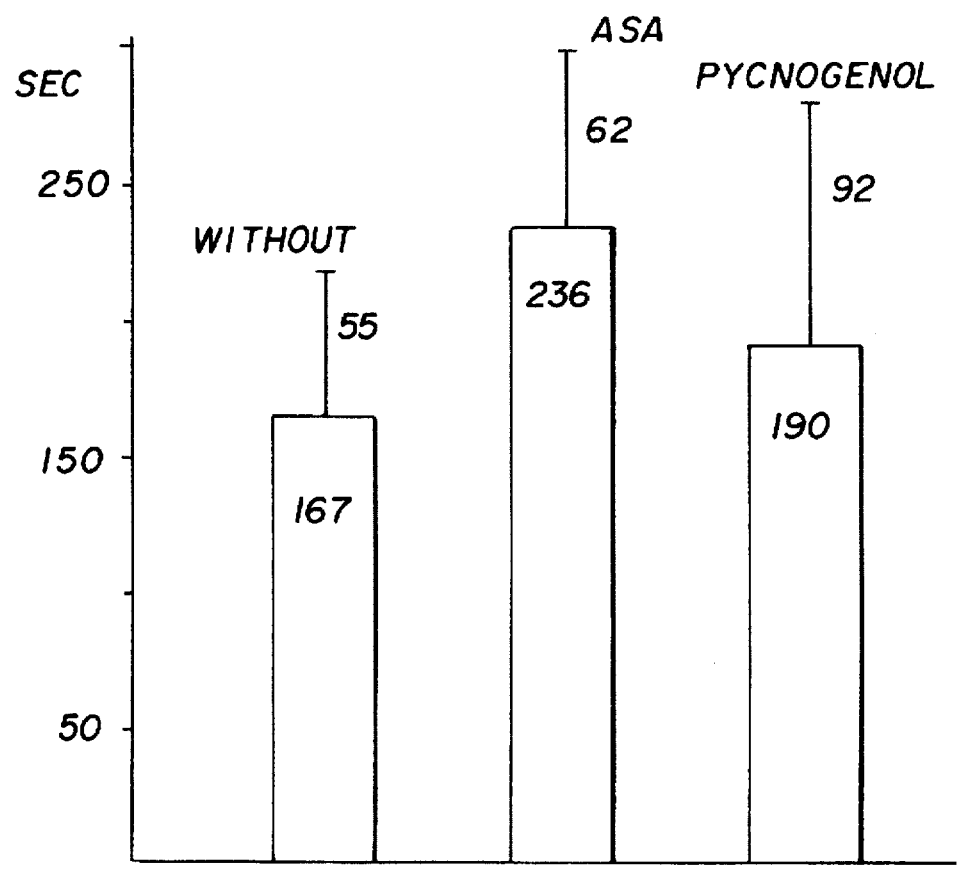
FIG. 2 is a graph showing the bleeding time following the administration of 500 mg ASA and Pycnogenol™ and without medication.

Bleeding time was determined following puncture of the ear lobe before smoking. FIG. 2 shows that bleeding times without medication and following intake of pine bark extract are not significantly different, however, following intake of ASA the bleeding time is significantly longer ($p=0.002$). The bleeding time following intake of 100 mg Pycnogenol™ is significantly shorter than after intake of 500 mg ASA ($p=0.02$).

The example demonstrates that Pycnogenol™ normalizes platelet aggregation in lower dose as compared to ASA, however, without affecting the bleeding time.

EXAMPLE 2

The following experiment was carried out to determine whether Pycnogenol™ can be used in suitable concentrations to inhibit adrenaline-induced platelet aggregation. Blood samples were collected from healthy volunteers and thrombocyte-enriched plasma was obtained by repeated centrifugation. The aggregation rate was measured by turbidimetry with and without preincubation with Pycnogenol™ in different concentrations following addition of adrenalin. The inhibition rate was calculated as given below.

$$\text{Inhibition rate} = \frac{\text{aggregation rate blank} - \text{aggregation rate pine bark extract}}{\text{aggregation rate pine bark extract}} \cdot 100$$

Figure 3:
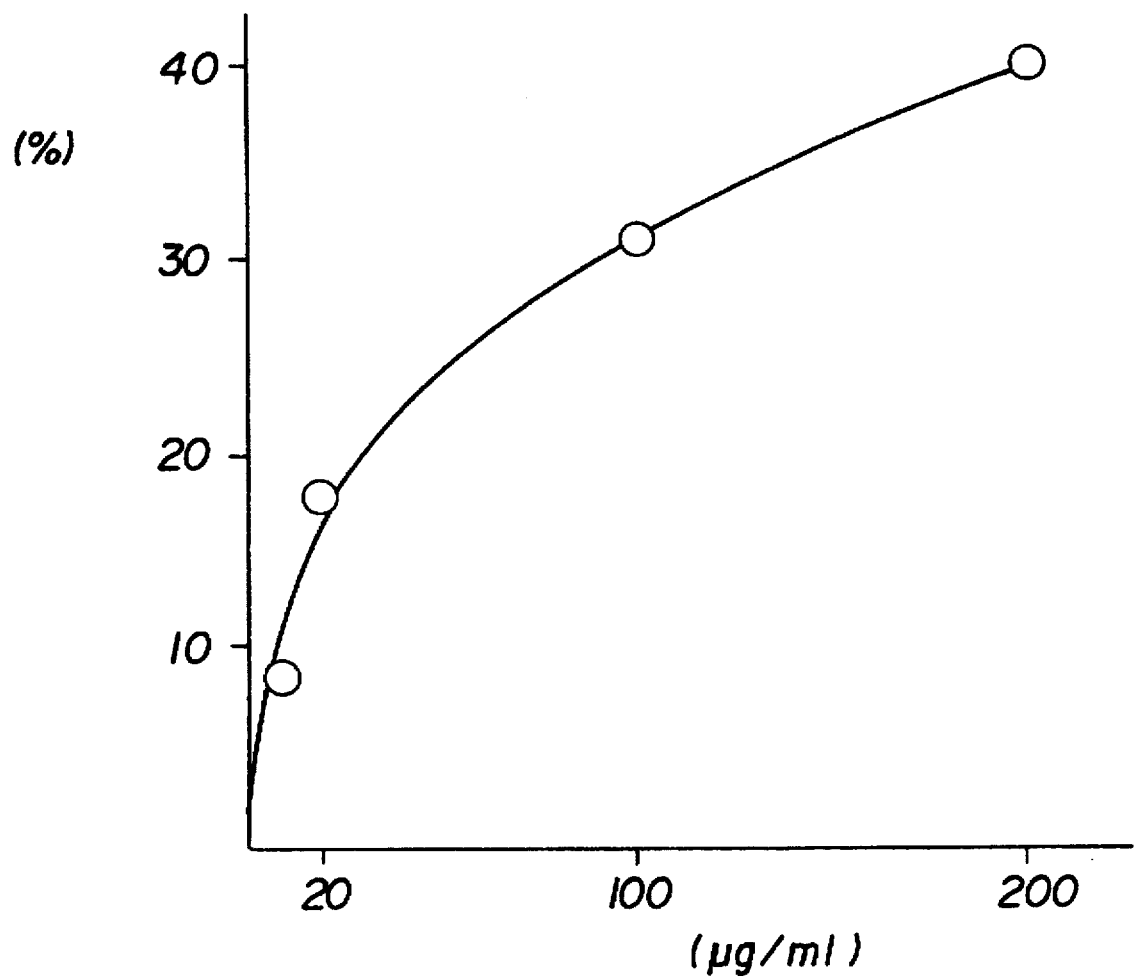
FIG. 3 is a graph showing the decrease of adrenaline-induced platelet reactivity following addition of pine bark extract in vitro.
Figure 1:
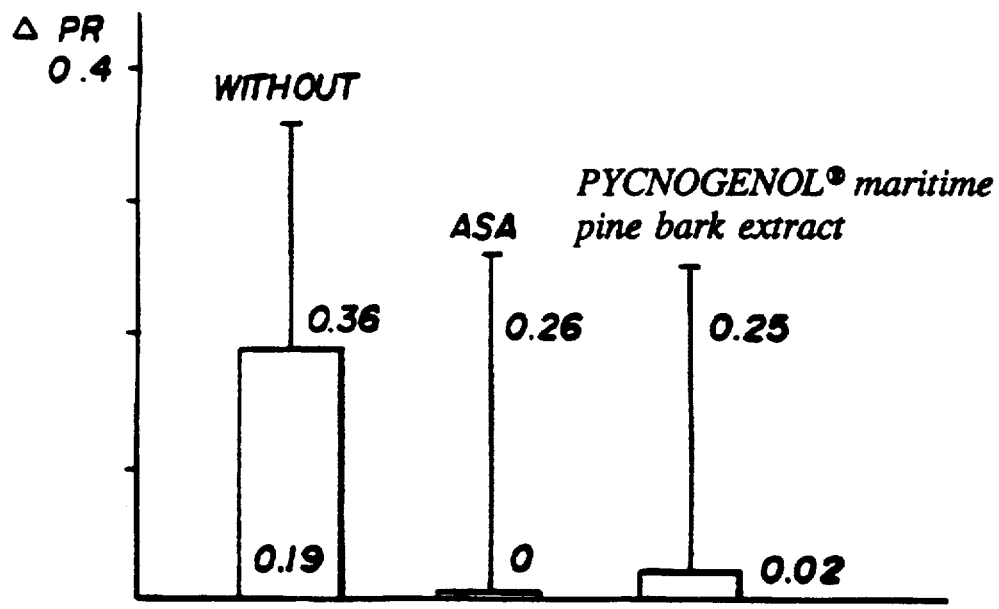
Figure 2:
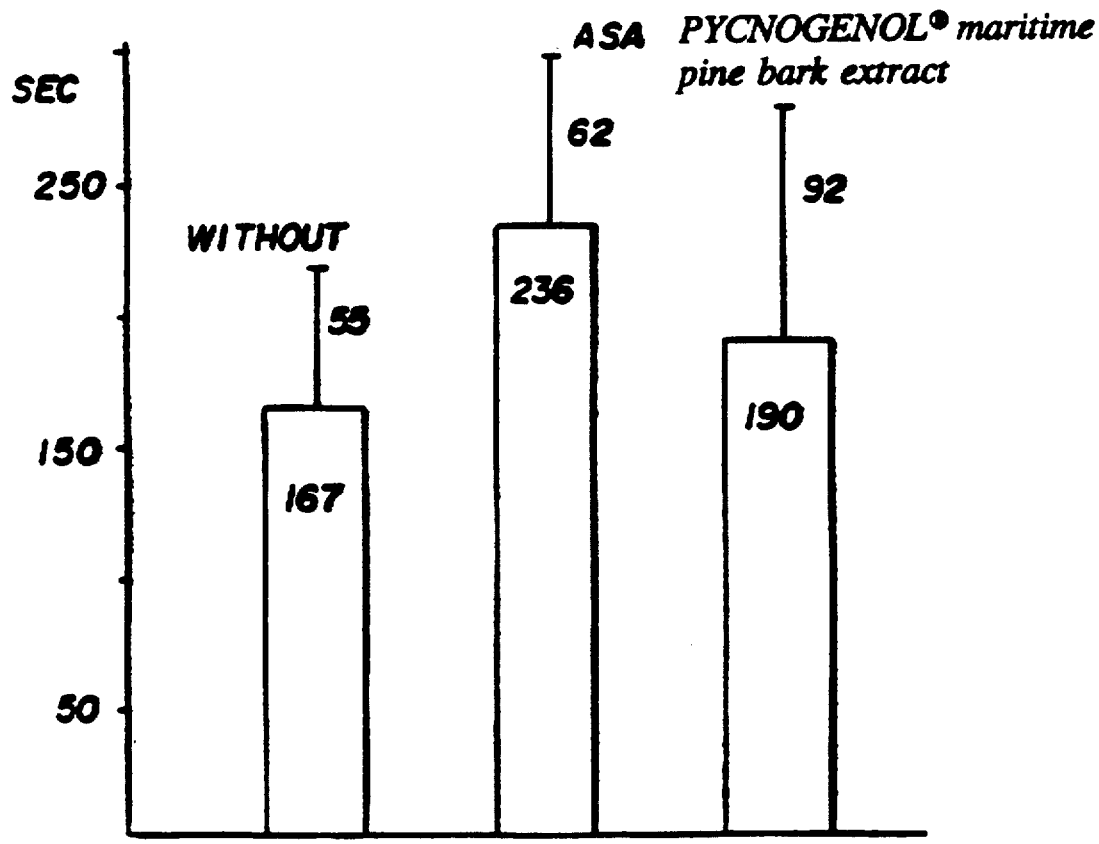

The example (FIG. 3) shows that Pycnogenol™ significantly inhibits platelet aggregation even in the presence of adrenaline.

I claim:

1. Method of controlling blood platelet aggregation induced by smoking or adrenaline in a human being comprising administering to a patient in need thereof 200 to 500 mg of extract of the bark of the maritime pine per day.

2. Method according to claim 1 wherein about 250 to 350 mg are administered per day.

3. Method according to claim 1 wherein oral administration is used.

4. Method according of claim 1 wherein single dose units of 50–150 mg are administered.

5. A method for reducing blood platelet aggregation induced by smoking or adrenaline in a human being comprising administering to a patient in need thereof a thromboxane biosynthesis inhibiting amount of extract of the bark of the maritime pine.

* * * * *

UNITED STATES PATENT AND TRADEMARK OFFICE
CERTIFICATE OF CORRECTION

PATENT NO. : 5,720,956
DATED : February 24, 1998
INVENTOR(S) : Peter Rohdewald

It is certified that error appears in the above-indentified patent and that said Letters Patent is hereby corrected as shown below:

Replace Figs. 1 and 2 of the drawings with Figs. 1 and 2 on the accompanying sheet.

UNITED STATES PATENT AND TRADEMARK OFFICE
CERTIFICATE OF CORRECTION

PATENT NO. : 5,720,956
DATED : February 24, 1998
INVENTOR(S) : Peter Rohdewald It is certified that error appears in the above-identified patent and that said Letters Patent is hereby corrected as shown below:

On the title page, item [54] and col 1, line 5;

In the title of the invention, cancel "(PYCNOGENOL)".

In the Abstract, line 2, delete "and enhance" and insert -- an enhanced --.

In Column 2, line 3 cancel "in the following referred to as Pycnogenol™" and insert -- commercially available under the trademark PYCNOGENOL®. PYCNOGENOL is a registered trademark of Horphag Research Limited. --.

In Column 2, line 5 cancel "Pycnogenol™" and insert -- Maritime pine bark extract --.

In Column 2, line 9 cancel "Pycnogenol™" and insert -- PYCNOGENOL® maritime pine bark extract --.

In Column 2, line 21 after the word methods, insert -- ,including those employing non-chlorinated solvents, --.

In Column 2, line 28 cancel "Pycnogenol™" and insert -- Maritime pine bark extract --.

UNITED STATES PATENT AND TRADEMARK OFFICE
CERTIFICATE OF CORRECTION

PATENT NO. : 5,720,956
DATED : February 24, 1998
INVENTOR(S) : Peter Rohdewald

It is certified that error appears in the above-indentified patent and that said Letters Patent is hereby corrected as shown below:

In Column 2, line 31 cancel "Pycnogenol™" and insert -- maritime pine bark extract --.

In Column 2, line 35 cancel "Pycnogenol™" and insert -- maritime pine bark extract --.

In Column 2, line 37 cancel "Pycnogenol™ and insert -- maritime pine bark extract --.

In Column 2, line 40 cancel "Pycnogenol™ and insert -- maritime pine bark extract --.

In Column 2, line 48 cancel "Pycnogenol™ and insert -- maritime pine bark extract --.

In Column 2, line 50 cancel "Pycnogenol™ and insert -- maritime pine bark extract --.

In Column 2, line 66 cancel "Pycnogenol™ and insert -- PYCNOGENOL® maritime pine bark extract --.

In Column 2, line 67 cancel "Pycnogenol™ and insert -- PYCNOGENOL® maritime pine bark extract --.

UNITED STATES PATENT AND TRADEMARK OFFICE
CERTIFICATE OF CORRECTION

PATENT NO. : 5,720,956
DATED : February 24, 1998
INVENTOR(S) : Peter Rohdewald

It is certified that error appears in the above-indentified patent and that said Letters Patent is hereby corrected as shown below:

In Column 3, line 4 cancel "Pycnogenol™" and insert -- PYCNOGENOL® maritime pine bark extract --.

In Column 3, line 11 cancel "Pycnogenol™" and insert -- PYCNOGENOL® maritime pine bark extract --.

In Column 3, line 12 cancel "(extract from the bark of the maritime pine)".

In Column 3, line 37 cancel "Pycnogenol™" and insert -- PYCNOGENOL® maritime pine bark extract --.

In Column 4, line 1 cancel "Pycnogenol™ and insert -- PYCNOGENOL® maritime pine bark extract --.

In Column 4, line 4 cancel "Pycnogenol™ and insert -- maritime pine bark extract --.

UNITED STATES PATENT AND TRADEMARK OFFICE
CERTIFICATE OF CORRECTION

PATENT NO. : 5,720,956
DATED : February 24, 1998
INVENTOR(S) : Peter Rohdewald

It is certified that error appears in the above-indentified patent and that said Letters Patent is hereby corrected as shown below:

In Column 4, line 11 cancel "Pycnogenol™ and insert -- maritime pine bark extract --.

In Column 4, line 16 cancel "Pycnogenol™ and insert -- PYCNOGENOL® maritime pine bark extract --.

In Column 4, line 24 cancel "Pycnogenol™ and insert -- maritime pine bark extract --.

Signed and Sealed this

Twenty-fifth Day of August, 1998

Attest:

BRUCE LEHMAN

*Attesting Officer*  *Commissioner of Patents and Trademarks*